United States Patent
Schwarz et al.

(10) Patent No.: US 9,089,568 B2
(45) Date of Patent: Jul. 28, 2015

(54) METHOD OF USING COMPATIBLE SOLUTES CONTAINING ECTOINE AND/OR HYDROXYECTOINE

(75) Inventors: Thomas Schwarz, Mannheim (DE); Georg Lentzen, Herdecke (DE); Jean Krutmann, Wegberg (DE)

(73) Assignee: Bitop AG, Witten (DE)

( * ) Notice: Subject to any disclaimer, the term of this patent is extended or adjusted under 35 U.S.C. 154(b) by 547 days.

(21) Appl. No.: 11/885,687

(22) PCT Filed: Mar. 13, 2006

(86) PCT No.: PCT/EP2006/002286
§ 371 (c)(1),
(2), (4) Date: Apr. 16, 2008

(87) PCT Pub. No.: WO2006/097263
PCT Pub. Date: Sep. 21, 2006

(65) Prior Publication Data
US 2009/0060876 A1    Mar. 5, 2009

(30) Foreign Application Priority Data
Mar. 12, 2005 (DE) .......................... 10 2005 011 442

(51) Int. Cl.
*A61K 31/505* (2006.01)
*A61K 31/66* (2006.01)
*A61K 31/683* (2006.01)
*A61K 31/7032* (2006.01)

(52) U.S. Cl.
CPC .............. *A61K 31/505* (2013.01); *A61K 31/66* (2013.01); *A61K 31/683* (2013.01); *A61K 31/7032* (2013.01)

(58) Field of Classification Search
CPC ............ A61K 2300/00; A61K 31/167; A61K 31/4406; A61K 31/53; A61K 31/549; A61K 31/7076; A61K 45/06; A61K 31/198; A61K 31/505; A61K 31/205; A61K 31/66; A61K 36/54; A61K 31/185; A61K 31/683; A61K 8/64; A61K 9/00
See application file for complete search history.

(56) References Cited

U.S. PATENT DOCUMENTS 5,789,414 A * 8/1998 Lapidot et al. ................ 514/256
5,834,473 A * 11/1998 Virtanen et al. ......... 514/266.22
5,880,098 A    3/1999 Haussinger
6,080,401 A * 6/2000 Reddy et al. .................. 424/93.3
7,147,849 B2  12/2006 Barth et al.
2003/0147937 A1 * 8/2003 Schwarz ...................... 424/439
2004/0028631 A1   2/2004 Schwartz
2007/0122464 A1   5/2007 Krutmann
2008/0014153 A1   1/2008 Schwartz
2011/0053896 A1   3/2011 Krutmann et al.
2011/0152294 A1   6/2011 Krutmann
2011/0207681 A1   8/2011 Klein
2013/0085149 A1   4/2013 Schmittmann

FOREIGN PATENT DOCUMENTS

DE    19925615 A1 * 12/2000
JP    19960188928   *  6/1996  ............. A61K 31/70
JP       10017478      1/1998
WO    WO 92/00744   *  1/1992  ............. A61K 31/66
WO    WO9200744         1/1992
WO    WO9738686      10/1997
WO    WO01/76572    10/2001

OTHER PUBLICATIONS

Arora et al, 2004. Inhibition of insulin amyloid formation by small stress molecules. FEBS Letters, vol. 564:121-125.*
NIH 2006. NIH Publication 06-3410, NIDDK, Crohn's Disease, pp. 1-7.*
Caprilli et al, 2008. Recent advances in the management of Crohn's disease. Digestive and Liver Disease, vol. 40:709-716.*
Juillerat et al, 2009. Appropriate maintenance treatment for Crohn's disease: Results of a multidisciplinary international expert panel—EPACT II. Journal of Crohn's and Colitis, vol. 3:241-249.*
Siccardi et al, 2005. Regulation of intestinal epithelial function: a link between opportunities for macromolecular drug delivery and inflammatory bowel disease. Advanced Drug Delivery Reviews, vol. 57: 219-235.*
Petros 2000. Crohn's disease update. Current Surgery, vol. 57(2):95-103.*
Jebbar et al, "Osmoprotection of *E. coli* by Ectoine: Uptake . . . ", J. of Bacteriology, Aug. 1992, p. 5027-5035.*
Abstract only, DERWENT-2001-062594. 2001.*
Klaus Unfried, et al. U.S. Appl. No. 14/323,017, filed Mar. 5, 2014 (not yet published).
Notice of Allowance issued May 6, 2014 in U.S. Appl. No. 10/563,586, filed Dec. 13, 2006.
Notice of Allowance issued Feb. 20, 2014 in U.S. Appl. No. 12/675,264, filed Oct. 5, 2010.
Klaus Unfried, U.S. Appl. No. 14/343,017, filed Mar. 5, 2014 (not yet published).

* cited by examiner

*Primary Examiner* — Debbie K Ware
(74) *Attorney, Agent, or Firm* — Berliner & Associates

(57) ABSTRACT

The invention relates to the use of compatible solutes, especially ectoine, hydroxyectoine, di-myo-inositol phosphate (DIP), cyclic 2,3 diphosphoglycerate (cDPG), 1,1-di-glycerol phosphate (DGP), β-mannosylglycerate (firoin), β-mannosylglyceramide (firoin A), proline betaine and/or derivatives as well as combinations thereof for the production of an agent aimed at preventing and treating gastrointestinal and amyloidal diseases, with agents containing said active ingredients being disclosed as well.

7 Claims, No Drawings

METHOD OF USING COMPATIBLE SOLUTES CONTAINING ECTOINE AND/OR HYDROXYECTOINE

This application is a 371 of PCT/EP06/02286 filed Mar. 13, 2006.

The invention relates to the use of compatible solutes, in particular ectoine, hydroxyectoine, di-myo-inositol phosphate (DIP), cyclic 2,3 diphosphoglycerate (cDPG), 1,1-diglycerol phosphate (DGP), β-mannosylglycerate (firoin), β-mannosylglyceramide (firoin A), proline betaine and/or derivatives as well as combinations thereof for the production of an agent aimed at preventing and treating gastrointestinal and amyloidal diseases, with agents containing said active substances being disclosed as well. The invention also relates to agents containing the microorganisms generating or enriching the above mentioned compatible solutes.

The world around us encompasses a multitude of different habitats. This includes biotopes which at first glance appear to be hostile but still accommodate living beings. Salt lakes, hot springs, cold deserts, geysers or other extreme place are examples of such inhospitable locations. Common to all these habitats is that they offer living conditions under which biological macromolecules and structures cannot exist without resorting to protective strategies.

Especially the microorganisms populating these habitats have developed a number of protective measures that enable them to survive. These microorganisms are known as extremophilic microorganisms.

One of the protective functions of extremophilic microorganisms is that they produce "compatible solutes". This class of substances is very heterogeneous and includes, aside from carbohydrates, also cyclic amino acids, organic phosphorous compounds and similar substances. Ectoine (2-methyl-4-carboxy-3,4,5,6-tetrahydropyrimidine), hydroxyectoine (2-methyl-4-carboxy-5-hydroxy-3,4,5,6-tetrahydropyrimidine), firoin (mannosylglycerate), firoin A (mannosylglyceramide), DGP (di-glycerol phosphate), cDPG (cyclic diphosphoglycerate), proline, proline betaine and DIP (di-myo-inositol phosphate) count among the typical compatible solutes produced by extremophilic microorganisms.

Compatible solutes are low-molecular, hydrophilic compounds of highly polar nature and thus excellently soluble in water. Compatible solutes produced by the applicant from extremophilic microorganisms are, for example:

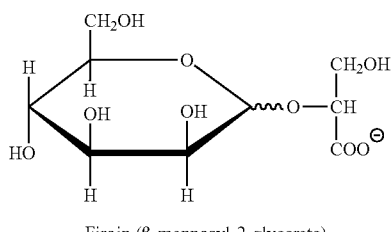

Firoin (β-mannosyl-2-glycerate)

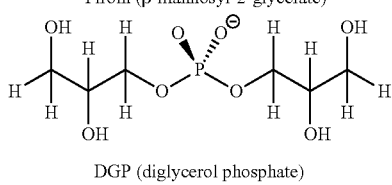

DGP (diglycerol phosphate)

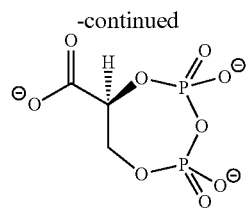

cDPG (cyclo-2,3-diphosphoglycerate)

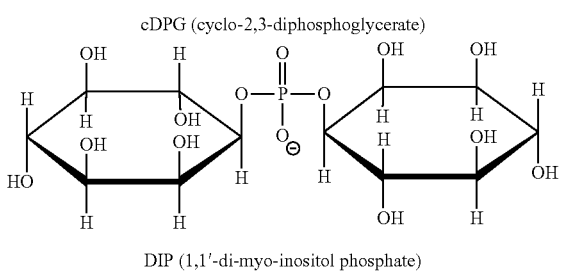

DIP (1,1'-di-myo-inositol phosphate)

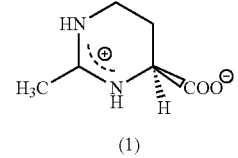

(1)

Ectoine ((S)-2-methyl-1,4,5,6-tetrahydropyrimidine-4-carboxylic acid)

The term "compatible solutes" describes the high degree of compatibility with the intracellular metabolism of microorganisms and thus the excellent agreeableness associated with it. This compatibility also exist in the event of very high concentrations in the molar range. The function of compatible solutes embraces the protection of biological structures against destructive effects.

These functions of the compatible solutes do not only take effect with the extremophilic microorganisms but also with mesophilic organisms and human beings. Here the protective functions are found in a number of guarding applications. Compatible solutes are used as skin protection agents (e.g EP 1 315 473 A or DE 100 44 985 A). Likewise, compatible solutes keep the protein structure stable, protect proteins against degradation reactions and stabilize solutions of proteins (for example in EP 0 671 161 A, US 2003157040 A or EP 1 is 127 141 A, also see Göller & Galinski, J. Molec. Catalysis B: 1999, 7, 3745).

A variety of synthetic and semi-synthetic components, but also microbiological fermentation products and microbially generated products are used as agents for oral ingestion in the form of a dietary supplement. Some examples of this are:

| | |
|---|---|
| Bacteria as supplement to human and animal foodstuff | GB 2 026 028 A |
| Beverages with amino acid blends | CN 1 117 824 A |
| Dietary supplement aimed at avoiding hair loss | US 512 23 69A |
| Dietary supplement having cancer prophylactical properties | CA 2 419 066 A |
| Dietary supplement for the alleviation of stress symptoms | EP 1 383 525 A |

In this context, great significance is attached to products stemming from mesophilic bacteria and fungi. Unknown, hitherto, has been the use of extremophilic microorganisms or compatible solutes or microbial extracts containing compatible solutes in agents intended for oral application as dietary supplement and for the prevention and therapy of diseases of the gastrointestinal tract.

Protective effects of compatible solutes on a cellular level can also be achieved at low concentrations (≤1 mM) in cell cultures (Bünger & Driller, Skin Pharmacol Physiol 2004; 17:232-237). Nevertheless, skin protective effects are only possible with higher concentrations because the repellent external apolar corneal layer of the skin must be overcome first and the resorption rate of the compatible solutes by the skin is only low.

When ingested orally a much better resorption of the ectoines can be expected resulting in the cells of the gastrointestinal tract to be protected directly.

These effects which are described in detail hereunder can also be put to commercial use by producing dietary supplements and pharmaceutical preparations specifically intended to positively influence the alimentation and health status of human beings and animals and by marketing the compatible solutes won from extremophilic microorganisms or the biomass of extremophilic microorganisms.

Proceeding from the above, the invention relates to the use of compatible solutes for prophylaxis and therapy as well as dietary supplements.

Therefore, an object of the invention relates as first mentioned above to the use of compatible solutes for the prevention and treatment of gastrointestinal and amyloidal diseases.

Another object of the invention are preparations containing the compatible solutes first mentioned above together with vitamins, mineral nutrients and/or customary additives. Another object of the invention are foodstuffs or nourishments having an appropriate compatible solute content.

Object of the invention is also an agent that contains microorganisms producing or enriching compatible solutes.

Preferred embodiments of the invention are the subject matter of subclaims.

According to the invention compatible solutes are in particular the species first mentioned above. Preferred compatible solutes according to the invention are ectoine and hydroxyectoine.

Surprisingly, it has now been determined that by the oral ingestion of "compatible solutes" and in particular of ectoine the course of chronically inflammable intestinal diseases can be favorably influenced. By way of a mouse model for Crohn's disease it could be verified that the severity and duration of the inflammation was favorably influenced by oral substitution providing the mice with "compatible solutes". Moreover, immunological investigations have shown that the TH-2 TH-1 approach typically adopted for the chronically inflammable intestinal disease may to some extent be circumvented by "compatible solutes". However, the positive effect of "compatible solutes" is not only limited to an alleviation of the symptoms of chronically inflammable intestinal diseases but in addition is characterized by a pronounced preventive potential. For example, a chronically inflammable disease induced through certain foodstuff constituents as, for example, particulate substances added to the food as bleaching agent could be significantly suppressed in the animal model if the animals for preventive purposes were initially treated by administering "compatible solutes" orally. It is to be assumed that such a preventive effect but also the therapeutic effect is primarily attributable to the anti-inflammatory properties of "compatible solutes" which on the one hand are aimed at the intestinal epithelial cell but also at the helper T lymphocytes deemed to be the cause of the pathogenesis.

It is known that compatible solutes stabilize proteins and inhibit the aggregation of proteins (Andersson et al. (2000) Biotechnol Appl Biochem 32 (Pt 3), 145-153; Borges et al. (2002) Extremophiles 6, 209-216). It is, furthermore, known that compatible solutes and in particular ectoine inhibit in vitro the formation of protein deposits, so-called amyloid fibrils (Arora et al. (2004) FEBS Leff 564, 121-125).

Amyloid fibrils consist of antiparallelly folded beta-leaflet structures and are characteristic of serious diseases such as Alzheimer's disease, type II diabetes, Parkinson's disease, AA amyloidosis, AL amyloidosis and ATTR amyloidosis, iatrogenic insulin dependent amyloidosis and many other diseases associated with the deposition of proteins.

Unexpectedly, it has now been ascertained from investigations with mice is involving the oral application of compatible solutes ectoine, hydroxyectoine and firoin A that this enabled the formation of amyloid plaques to be reduced. Likewise, through the administration of compatible solutes the occurrence of neuropathologic effects could be reduced. The occurrence of amyloid diseases could be significantly inhibited in the animal model if the animals, for preventive purposes, were treated before by administering "compatible solutes" orally. It is to be assumed that such a preventive effect but nevertheless the therapeutic effect as well is primarily attributable to the amyloid-inhibiting properties of "compatible solutes".

Surprisingly, it has also been found that the compatible solute ectoine also occurred in food the production processes of which inter alia take place in extreme (e.g. highly saline) environments and involve microbial processes. It could thus be verified that the surface of certain cheese types such as Harzer cheese or Limburger cheese showed significant and well provable ectoine concentrations. Ectoine was also detected in the interior of the mentioned cheese types. This substantiates the new findings that the compatible solutes of extremophilic microorganisms, such as for example, ectoine, have been part of the human food chain for centuries.

According to the invention, an orally administered pharmaceutical form is described in which compatible solutes, especially ectoine and hydroxyectoine, or preparations of microorganisms containing compatible solutes, in particular

*Brevibacterium* spec.
*Halomonas* spec.
*Rhodothermus* spec.
*Pyrococcus* spec.
*Marinococcus* spec.

are used as dietary supplements or as pharmaceuticals for the treatment of gastrointestinal diseases. Without limiting the scope of the invention in any aspect the pharmaceutical form, due to the physicochemical properties of the compatible solutes, may, for example, be a powdery blend, a tablet, a paste or a concentrated solution, either in the form of extracts of microorganisms, living or deadened microorganisms, mixtures or as a pure substance.

Combinations with other substances are also conceivable as long as they do not negatively interact with each other. Accordingly, in agents intended for oral use compatible solutes or preparations of microorganisms containing compatible solutes may be combined with extracts of herbs and fruit such as Islandic moss, rampion, cinnamon, yarrow, star-anise, sage, rosemary, pimento, peppermint, oregano, clove, dandelion, lovage, lavender, raspberry, ginger, camomile, cardamom, coriander, caraway, curcuma, basil, summer savory. Furthermore, compatible solutes containing agents for oral use may be combined with natural oils such as evening primrose oil, salmon oil and other fish oils. Other substances with which the compatible solutes or preparations containing compatible solutes may be combined are minerals (zinc, sodium, potassium, calcium, magnesium, selenium, chromium, iron, cobalt, copper, manganese, silicon, zinc), vitamins (vitamin A, vitamin D, vitamin E, vitamin K, vitamin B1, vitamin B2, niacin, vitamin B6, pantothenic acid, biotin, folic acid, vitamin B12, vitamin C), L-carnitine and isoflavones.

The compatible solutes may also be combined with solid food. This is particularly expedient if, for examples, the solutes are admixed in the form of a highly concentrated aqueous solution and subsequently dried. Due to the thermal stability a use in pastries is also possible.

The concentration of the compatible solutes in this context ranges between 0.01 and 50%. The daily dose usually is in the range of between 1 and 2,000 mg per kg of body weight and may greatly vary to suit the relevant application.

The agents containing compatible solutes may be tablets, dragées, capsules, powders, granulates, lozenges, aqueous solutions, liquid ampoules and suppositories. The agents may also constitute microorganisms as well as extracts and preparations of microorganisms containing compatible solutes. In particular, the agents may contain extracts of foodstuff as well as extracts and preparations of microorganisms occurring in food. The amount of compatible solutes in this case comes to at least 100 mg of active substance per dosage unit (application/administration unit), expediently 200 to 500 mg.

According to the invention, compatible solutes for oral use such as ectoine, hydroxyectoine, mannosylglycerate, mannosylglyceramide, di-glycerine phosphat, cyclic diphosphoglycerate, proline, proline betaine and di-myo-inositol phosphate may be won from microorganisms and other biological sources. The microorganisms may be members of the genus *Brevibacterium, Vibrio, Bacillus, Halomonas, Planococcus, Sporosarcina* and *Marinococcus handeln*. Especially preferred are the use of microorganisms that synthesize ectoine and hydroxyectoine and are found in foodstuff such as *Brevibacterium linens, Brevibacterium casei, Vibrio costicola, Halomonas elongata*. The substances may be won by treating the cells with a wash solution consisting of water, volatile matter and/or substances having a stabilizing effect on the cells. The agent meant for oral application may either be produced from washed, dried cells or isolated from cells by way of an osmotic shock.

Alternatively, the compatible solutes may be produced by chemical synthesis.

As provided for by the invention the compatible solutes and preparations from extremophilic microorganisms containing compatible solutes may be used as dietary supplements, dietetic foodstuff or supplementing balanced diets as well as for the prevention and treatment of diseases, in particular diseases of the gastrointestinal tract, as for example Crohn's disease.

Further embodiments of the invention relate to the use of extracts and concentrates obtained from foodstuff containing compatible solutes.

In any case the invention is based on the fact that the compatible solutes, as defined hereinbefore, are suited as active substances to positively influence numerous body functions and metabolic processes, especially with respect to the gastrointestinal tract. Insofar the object of the invention is the use of said active substances as dietary supplements and in the field of medical prophylaxis and therapy.

The invention claimed is:

1. A method for therapy of chronically inflammable intestinal diseases, comprising administering to a human a compatible solute selected from a group consisting of ectoine, hydroxyectoine and combinations thereof to treat a chronically inflammable intestinal disease.

2. The method of claim 1, wherein the inflammable intestinal disease is Crohn's disease.

3. The method of claim 1 or 2 wherein administering is performed orally or rectally.

4. The method of claim 1, wherein the solute is provided in an amount ranging between 1 and 2000 mg of said compatible solute per kg of body weight per day.

5. The method of claim 1, wherein the solute is in dried or freeze-dried form.

6. The method of claim 1, wherein the solute is in the form of powder, tablets or capsules.

7. The method of claim 4, wherein the solute is provided in an amount ranging between 10 to 100 mg of said compatible solute per kg of body weight per day.

* * * * *